US005888552A

United States Patent [19]
Bounous et al.

[11] Patent Number: 5,888,552
[45] Date of Patent: Mar. 30, 1999

[54] ANTI-CANCER THERAPEUTIC COMPOSITIONS CONTAINING WHEY PROTEIN CONCENTRATE

[75] Inventors: Gustavo Bounous, Monteal; Phil Gold, Westmount, both of Canada

[73] Assignee: Immunotec Research Corporation Ltd., Quebec, Canada

[21] Appl. No.: 381,975

[22] PCT Filed: Aug. 5, 1993

[86] PCT No.: PCT/CA93/00309

§ 371 Date: May 8, 1995

§ 102(e) Date: May 8, 1995

[87] PCT Pub. No.: WO94/04168

PCT Pub. Date: Mar. 3, 1994

Related U.S. Application Data

[63] Continuation-in-part of Ser. No. 929,347, Aug. 13, 1992, abandoned, and Ser. No. 866,756, Apr. 10, 1992, Pat. No. 5,456,924, which is a continuation-in-part of Ser. No. 417, 246, Oct. 4, 1989, Pat. No. 5,290,571, which is a continuation-in-part of Ser. No. 289,971, Dec. 23, 1988, abandoned, which is a continuation-in-part of Ser. No. 188,276, Apr. 29, 1988, abandoned, said Ser. No. 929,347, is a continuation-in-part of Ser. No. 417,246.

[51] Int. Cl.$^6$ ..................................................... A61K 35/20
[52] U.S. Cl. .............................. 424/535; 514/2; 514/21; 514/251; 514/276; 514/885; 530/365; 530/833; 426/72
[58] Field of Search .................................. 424/535; 514/2, 514/21, 251, 276, 885; 530/365, 833; 426/72

[56] References Cited

U.S. PATENT DOCUMENTS 4,784,685  11/1988  Meister .................................... 504/110

FOREIGN PATENT DOCUMENTS 222560   5/1981   Argentina .
1495940  12/1977  United Kingdom .

OTHER PUBLICATIONS

Anderson, M.E., "Tissue glutathione", *C.R.C. Handbook of Methods for Oxygen Radical Research*, pp. 317–329 (1985) (Exhibit 1).
Lauterburg, B.H. et al., "Therapeutic doses of acetaminophen stimulate the turnover of cysteine and glutathione in man", *J. Hepatol.*, vol. 4, pp. 206–211 (1987) (Exhibit 2).
Lewis, A.D. et al., *Proc. Natl. Acad. Sci.*, vol. 85, pp. 8511–8515 (1988) (Exhibit 3).
Russo, A. et al., "Selective modulation of glutathione levels in human normal versus tumor cells and subsequent differential response to chemotherapy drugs", *Cancer Res.*, vol. 46, pp. 2865–2848 (1985) (Exhibit 4).
Walstra, P.J., "Dairy Chemistry and Physics", Wiley J. Nitork, (ed.), p. 106 (1984) (Exhibit 5).

Williamson, J.M. et al., "Intracellular cysteine delivery system that protects against toxicity by promoting GSH synthesis", *Proc. Natl. Acad. Sci. U.S.A.*, vol. 79, pp. 6246–6249 (1982) (Exhibit 6).
Bounous, G., et al., "Dietary Whey Protein Inhibits the Development of Dimethylhydrazine Induced Malignacy." *Clin. Invest. Med.*, (1980) vol. 11, pp. 231–217.
Papenburg, R., et al., "Dietary Milk Proteins Inhibit The Development of Dimethylhydrazine–Induced Malignacy." *Tumor Biology*, (1990) vol. 11, pp. 129–136.
Baruchel, S., et al., (1992) AACR Abstract, "Different Effects of OTZ on Organ GSH Levels in Rate Bearing Tumors".
John, A.M, et al., "Amino Acid Requirements of the Growing Mouse." *J. Nutr.*, (1976) vol. 106, pp. 1361–1367.
Hoag, W.G., et al., "Nutrition" In: *Biology of the Laboratory Mouse*, E.L. Green, (ed.), (McGraw–Hill, New York: 1966) pp. 39–43.
Cunnigham, A., et al., "Further Improvements in the Plaque Technique for Detecting Single Antibody Forming Cells." *J. Immun.*, (1968) vol. 14, pp. 559–600.
Anderson, M.E., "Tissue Clutathione" In: Handbook of Methods for Oxygen *Radical Research*. (C.R.C. Press, Boca Raton: 1988) pp. 317–329.
Glatt, H., et al., "Mutagenicty of Glutathione and Cysteine in the Ames Test." *Science*, (1983) vol. 220, pp. 961–962.
Taylor, Y.C., et al., "Elevation of Intracellular Glutathione Levels Following Depletion and its Relationship to Protection Against Radiation and Alkylating Agents." *Pharmacol. Ther.*, (1988) vol. 39, pp. 293–299.
White, C.W., et al., "Hypoxia Increases Glutathione Redox Cycle and Protects Rat Lungs Against Oxidates." J. Appl. Physiol., (1988) vol. 65, pp. 2607–2616.
Anderson, M.E., et al., "Transport and Direct Utilization of Gamma–Glutamylcyst(e)ine for glutathione Sythesis." *Proc. Natl. Acad. Sci. U.S.A.*, (1983) vol. 80, pages 707–711.
Richie, J.P., et al., "Correction of a Glutathione Deficiency in the Aging Mosquito Increses its Longevity." *Proc. Soc. Exp. Biol. Med.*, (1987) vol. 184, pp. 113–117.
Fernandez–Checa, J.C., et al., "Effects of Chronic Ethanol Feeding on Rat Hepatocyte Glutathione." *J. Clin. Invest.*, (1989) vol. 83, pp. 1247–1252.
Meister, A., et al., "Glutathione." *Ann. Rev. Bloch.*, (1983) vol. 52, pp. 711–760.
Hamilton, T.C., et al., "Augmentation of Adriamycin, Melphalan and Cisplastin Cytoxicity in Drug Resistant and Sensitive Human Ovarian Cancer Cell Lines by BSO Mediated GSH Depletion." *Biochem. Pharm.*, (1985) vol. 34, pp. 2583–2586.

(List continued on next page.)

*Primary Examiner*—Jean C. Witz
*Attorney, Agent, or Firm*—John P. White; Cooper & Dunham LLP

[57] ABSTRACT

This invention relates to a method of treatment of patients having lesions resulting from cancer cells and to an application as an anti-cancer composition of undenatured whey protein concentrate.

22 Claims, 3 Drawing Sheets

OTHER PUBLICATIONS

Suzukake, K., et al., "Dechlorination of L–Phenylalanine Mustard by Sensitive and Resistant Tumor Cells and its Relationship to Intracellular Glutathione Content." Biochem. Pharm., (1983) vol. 32, pp. 165–171.

Enker, W.E., et al., "Experimental Carcinogenesis of The Colon Induced by 1,2–Dimethylhydrazine–di HC1: Value as a Model of Human Disease." J. Surg. Res., (1976) vol. 21, pp. 291–299.

Corbett, T.H., et al., "Evaluation of a Single Agent and Combination of Chemotherapeutic Agents in Mouse Colon Carcinogenesis." Cancer, (1977) vol. 40, pp. 2650–2580.

Bounous, G., et al., "The Biological Activity of Undenatured Dietary Whey Proteins: Role of Glutathione." Clin. Inves. Med., (1991) vol. 14, pp. 269–309.

Bounous, G., et al., "Immunoenhancing Property of Dietary Whey Protein in Mice: Role of Glutathione." Clin. Invest. Med., (1989) vol. 12, pp. 154–161.

Meister, A., 5–Oxoprolinuria and Other Disorders of Glutathione Biosynthesis. In: Metabolic Basis of Inherited Diseased (Stranbury J.B. et al., eds.) (4th edn. McGraw Hill, 1978) pp. 328–335.

Bounous, G., et al., "The Immunoehancing Property of Dietary Whey Protein Concentrate." Clin. Invest. Med., (1988) vol. 11, 271–278.

Hirai, Y., et al., "Report: Evaluation of the Immunological Enhancement Activities of Immunocal." Otsuka Pharmaceutical Co. Ltd: Cellular Technology Institute: Dec. 13, 1990, Osaka, Japan.

Rous, P., "The Influence of Diet on Transplanted and Spontaneous Mouse Tumors." J. Exper. Med., (1914) vol. 20, pp. 433–451.

White, R.F., et al., "Source of Tumor Proteins. Effect of a Low–Nitrogen Diet on the Establishment and Growth of a Transplanted Tumor." J. Natl. Cancer Inst., (1945) vol. 5, pp. 261–263.

Hawrylewics, E.J., et al., "Dietary Protein, Enhancement of N–Nitrosomethyl Urea–Induced Mammary Carcinogenesis, and Their Effect on Hormone Regulation in Rats." Cancer Res., (1986) vol. 46, pp. 4395–4399.

Visek, W.J., "Dietary Protein and Experimental Carcinogenesis." Adv. Exp. Biol., (1986) vol. 206, pp. 163–186.

Jacquet, J., et al., "Nutrition et Cancer Experimental: Cas du Lait." C.R. Hed. Seanc. Acad. Agric. de France, (1968) vol. 54, pp. 112–120.

Hirayama, T., "The Epidemiology of Cancer of the Stomach in Japan with Special Reference to the Role of Diet", Presented at the International Cancer Congress Tokyo, Japan 1966.

IRAC International Microecology Group, Dietary Fiber, Transit–Time, Fecal Bacteria Steriods, and Colon Cancer in Two Scandinavian Populations. The Lancet II, (1977) pp. 207–211.

Raddy, G.V., et al., "Antitumor Activity of Yogurt Components." J. Food Protect., (1983) vol. 46, pp. 8–11.

Nutter, R.L., et al., "Modification of Transplantable Colon Tumor and Immune Responses in Mice fed Different Sources of Protein, Fat and Carbohydrate." Cancer Letters, (1983) vol. 18, pp. 49–62.

Gridley, D.S., et al., "Modification of Herpes 2–Transformed Cell–Induced Tumors in Mice Fed Different Sources of Protein, Fat and Carbohydrate." Cancer Letters, (1982) vol. 17, pp. 161–173.

Nutter, R.L., et al., "Balb/c Mice Fed Milk or Beef Protein: Differences in Response to 1,2–Dimethylhydrazine Carcinogenesis." J.N.C.I., (1983) vol. 71, pp. 867–874.

Tsuru, S., et al., "Inhibition of Tumor Growth by Dairy Products." J. Clin. Lab. Immunol., (1988) vol. 25, pp. 177–183.

Bourtourault, M., et al., "Effet des Proteins du Lactoserum Bovin sur la Multiplication de Cellules Cancereuses Humaines." C.R. Soc. Biol., (1991) vol. 185, pp. 319–323.

Laursen, I., et al., "Serum Albumin as a Modulator of Growth of the Human Breast Cancer Cell line MCF–7." Anti–Cancer Res., (1990) vol. 10, pp. 343–351.

Bounous, G., et al., "Whey Proteins in Cancer Prevention." Cancer Letters, (1991) vol. 57, pp. 91–94.

Mekhail–Ishak, K., et al., Drug Metabolizing Enzymes in Human Colon Cancer: Implications for Therapy. Cancer Res. (In Pres.), 1989.

Swaisgood, M.E., "Characteristics of Edible Fluids of Animal Origin: Milk" In: Food Chemistry, O.R. Fennema, (ed.), (Marcel Dekker, Inc.: 1985) pp. 791–826.

Puri, R.N., et al., "Transport of Glutathione as Gamma–Clutamycysteinyl–Clycylester, into Liver and Kidney." Proc. Natl. Acad. Sci. U.S.A., (1987) vol. 80, pp. 5258–5260.

ANTI-CANCER THERAPEUTIC COMPOSITIONS CONTAINING WHEY PROTEIN CONCENTRATE

RELATED APPLICATIONS

This application is a 371 of PCT/CA93/00309, filed Aug. 5, 1993 which is a Continuation-in-Part of U.S. Ser. No. 07/929,347, filed Aug. 13, 1992, now abandoned, which is a CIP of U.S. Ser. No. 07/417,246 filed Oct. 4, 1989, now U.S. Pat. No. 5,290,571 which is a CIP of U.S. Ser. No. 07/289,971, filed Dec. 23, 1988, now abandoned, which in turn, is a CIP of U.S. Ser. No. 07/188,276, filed Apr. 29, 1988, now abandoned. This application is also a CIP of U.S. application Ser. No. 07/866,756, filed Apr. 10, 1992, now U.S. Pat. No. 5,456,924 which is a CIP of U.S. application Ser. No. 07/417,246 filed Oct. 4, 1989, now U.S. Pat. No. 5,290,571 which is a CIP of said U.S. Ser. No. 07/289,971, filed Dec. 23, 1988, now abandoned, which is a CIP of Ser. No. 07/188,276, filed Apr. 29, 1988, now abandoned. The contents of those applications are included by reference in their entirety.

SUMMARY OF THE INVENTION

The present invention is based on the surprising discovery that undenatured whey protein concentrate has an enhanced immunological effect. More specifically, this invention relates to the effect of the oral administration of undenatured whey protein concentrate (WPC) on host resistance to the development of chemically induced cancer and also the effect of such oral administration on the inhibition of cancer.

In U.S. application Ser. No. 298,971 and Ser. No. 417, 246, and also in Bounous et al "Dietary Whey Protein Inhibits the Development of Dimethyl-hydrazine induced Malignancy" (1) we described experiments showing that continuous feeding of WPC in the diet inhibits the development (number and size of tumours) in the colon of a mouse over a period of 24 weeks of dimethylhydrazine (DMH) treatment. This anti-tumour effect could be caused by increased resistance of target cells to the carcinogen and/or a direct inhibitory effect of WPC on the cancer cells. A subsequent series of experiments (2) where animals were fed Purina diet for the first 20 weeks of DMH and then switched to WPC diet for the remaining 8 weeks of DMH treatment, suggested some inhibitory effect of WPC feeding on cancer cells.

Most recently (3) a group of French scientists confirmed in vitro a direct inhibitory effect of WPC on human cancer cells. Indeed similar studies in vitro with human breast cancer cells have shown that bovine serum albumin (BSA) is the factor exerting inhibition of cancer cell replication (4).

We have also shown that this activity of WPC is specifically dependent upon the glutamylcysteine groups (substrate for GSH synthesis) present in the BSA fraction of WPC (U.S. Ser. No. 563,794). Interestingly, the introduction of the cysteine delivery system ozothiazolidine-4-carboxylate (OTZ) (ozothiazolidine-4-carboxylate), while enhancing glutathione (GSH) levels in normal cells, was found to result in feedback inhibition of the GSH cycle in human tumour cells (5). This differential effect of OTZ was recently confirmed in vivo (6). The previously described direct inhibitory effect of WPC (3) and more specifically of BSA (4) could be explained therefore by the release during incubation of a potent cysteine delivery system such as glutamylcysteine.

We have therefore reached the following conclusions:

1) BSA is the protein fraction of WPC that we found to be primarily responsible for the GSH promoting activity of WPC. This activity which we believe to be the basis for the immuno enhancing and anticarcinogen effect of WPC, is specifically dependent upon the glutamylcysteine groups (substrate for GSH synthesis) present in the BSA fraction of WPC.

2) The molecular weight of BSA is 66,267 hence quite different from the KW of the anti-cancer factor patented by Villadsen (MW 500–20,000). (7).

3) Our earlier findings (1,2) could be explained as follows: During DMH treatment, WPC feeding, by increasing cellular GSH, protects the target cells against the effects of the carcinogen. In addition, increased availability of substrate for GSH synthesis could inhibit replication of formed cancer cells.

4) We have now established the importance of a high level of serum albumin (BSA) in the WPC in providing a substrate for GSH synthesis. We can conclude that dietary whey protein concentrate in undenatured form and containing $\geq 10\%$ BSA exerts an anti-tumour effect.

DETAILED DESCRIPTION

Definitions (a) Whey Protein

Whey proteins are the group of milk proteins that remain soluble in "milk serum" or whey after precipitation of caseins at pH 4.6 and 20° C. The major whey proteins in cow's milk are beta-lactoglobulin ($\beta$ L), alpha-lactalbumin ($\alpha$ L), immunoglobulin and serum albumin (SA).

The product of industrial separation of this protein mixture from whey is called "whey protein concentrate" (WPC) or isolate. The WPC that was used in most of our early experiments is from bovine milk (Lacprodan-80 from "Danmark Protein A.S."). Use in its undenatured state is indicated as U-Lacp, and in its denatured state is indicated as D-Lacp. Lactalbumin (L) is the term traditionally used to define WPC.

(b) c=casein;

(c) SRBC=Sheep red blood cells;

(d) PFC=Plaque forming cells (spleen): enumeration of PFC in spleen is used to assess the humeral immune response to SRBC injection;

(e) GSH=Glutathione (L-gamma-glutamyl-L-cysteinylglycine);

(f) DMH=1,2-Dimethylhydrazine;

(g) The defined formula diets tested varied only in the type of protein;

(h) Whey of bovine milk contains approximately 6 g per liter protein, most of the lactose, mineral and water soluble vitamins.

Diets Used in These Studies
Referred to below in Table 3

Diets are prepared in the following way: 20 g of selected pure protein, 56 g of product 80056 protein free diet powder containing corn syrup, corn oil, tapioca starch, vitamins and minerals (Mead-Johnson Co. Inc., U.S.A.), 18 g cornstarch, 2 g wheat bran; 0.05 g Nutramigen vit-iron premix (Bristol-Myers, Ontario, Canada), 2.65 g KCl; 0.84 g NaCl. The carbohydrate and lipid components of our formula diets were the same. The only variable in the various purified diets was the type of protein (20 g protein/100 g diet). At this concentration in diet all the different proteins tested provided the daily requirements of essential amino acids for the growing mouse (8).Vitamins and minerals were the same in each set of experiments and were added in the amount necessary to provide daily requirements for the growing mouse (9, 10). Table 1, below, indicates the variation in suggested vitamin requirements for mouse diets and their contents in some of our formulations. Therefore all the formula diets used in our experiments were designed to provide adequate nutrition as demonstrated by normal body growth, serum protein (9) and by the absence of hair loss, dermatitis, cataract, ataxia, fatty liver etc. The latter symptoms were of course present in very old mice and were related to the aging process.

Immunization for Plaque Assays

The diet-fed mice were immunized by an intravenous injection of $5 \times 10^6$ washed sheep red blood cells obtained weekly from Institut Armand-Frappier, Laval des Rapides, Quebec, Canada.

Plaque Forming Cell (PFC) Assay

The method used for assaying IgM plaque forming cells was essentially the one described by Cunningham and Szenberg (11), with certain minor modifications. Spleen cell suspensions were prepared by gently tamping the spleen through a 50-mesh stainless steel screen, and collecting the cells in balanced salt solution (BSS) supplemented with 10% heat-inactivated calf serum (Grand Island Biological Company, Montreal, Quebec, Canada). The spleen cells were washed and made up to 15 ml with BSS. Sheep red blood cells were washed twice and made up to a 20% concentration. Guinea pig serum (Grand Island Biological Company, Montreal, Quebec, Canada) as a source of complement was diluted 1/15 with BSS. All stock solutions were kept on ice water until used. The test consisted of mixing 0.05 ml of spleen cells, 0.15 ml of sheep red blood cells and 0.75 ml of the complement solution in a test tube at 37° C. The whole mixture was immediately withdrawn

TABLE 1

VITAMIN AND MINERAL CONTENT OF TEST DIETS (amount/100 g diet)

|  |  | TEST DIETS | JACKSON (9) (range of amount recommended in Jackson laboratories diets) |  |
|---|---|---|---|---|
| VITAMINS: |  |  |  | AIN 76(10) |
| Vitamin A, IU | 1295 | 1800 | 24–550 | 400 |
| Vitamin D, IU | 260 | 360 | 14–506 | 100 |
| Vitamin E, IU | 11.6 | 18 | 1–2.7 | 5.0 |
| Vitamin K, mg | 0.06 | 0.09 | — | 0.005 |
| Thiamine (Vitamin B1), mg |  | 0.34 | 0.63 0.22–.99 | 0.60 |
| Riboflavin (Vitamin B2), mg |  | 0.38 | 0.69 0.24–1.1 | 0.60 |
| Vitamin B6, mg | 0.26 | 0.36 | 0.1–0.55 | 0.70 |
| Vitamin B12, mg | 0.0012 | 0.054 | .0039–.0055 | 0.001 |
| Niacin, mg |  | 5.1 | 9.2 26–143 | 3.0 |
| Foilc add, mg | 0.063 | 0.12 | 0.05–0.27 | 0.2 |
| Pantothenic acid, mg | 1.93 | 3.38 | 1–5.5 | 1.6 |
| Biotin, mg |  | 0.031 | 0.058 0.019–0.165 | 0.02 |
| Vitamin C, mg | 53.3 | 65 | — | — |
| Choline, mg |  | 44 | 76 49–145 | 100 |
| Inositol, mg |  | 19.8 | 19.8 — | — |
| MINERALS: |  |  |  | AIN 76 |
| Calcium, mg |  | 430 | # | 520 |
| Phosphorus, mg | 260 ........# |  |  | 400 |
| Magnesium, mg | 63.2 ........# |  |  | 50 |
| Iron, mg |  | 7.9 |  | 3.5 |
| Zinc, mg |  | 3.57 | # | 3.0 |
| Copper, mg |  | 0.47 | # | 0.60 |
| Iodine, mg |  | 0.023 |  | 0.02 |
| Sodium, mg |  | 232 |  | 100 |
| Potassium, mg | 997 |  |  | 360 |

After Minerals Analysis
(9) Hoag W. G., Dickie M. M. "Nutrition: in Green E. L. (Ed) Biology of the Laboratory Mouse McGraw-Hill NY 1966 pp 39–43. (Jackson was our supplier).
(10) The Mouse in Biomedical Research, vol III Eds Foster-H. L., Seall J. D., Fox J. B., Academic press 1983, NY pp 57–58 and put into slide chambers, sealed with warm paraffin wax, and incubated at 37° C. for 45 to 60 min. The number of plaque forming cells was counted and their total number per spleen estimated by multiplying the number of plaque forming cells in each sample (0.05 ml spleen cells) by 300. The values are expressed per total organ rather than per $10^6$ spleen cells, since this appears to reflect more accurately the functional status of the spleen per se.

Mice were assayed for the plaque forming cell response to sheep red blood cells normally on the fifth day after immunization when the response was shown to peak or, in the kinetic study, on days 3, 4, 5 and 6 post-immunization.

Statistics

The mean plaque forming cell values were compared among the dietary groups using either Student's test, when two groups were being compared, or the analysis of variances (ANOVA) for more than two groups. Because of the heterogeneity of variances among groups, the adjustment given by Brown and Forsythe was used.

Spleen Glutathione Content

Ninety milligrams of mouse spleen were weighed using a Mettler PM-300 balance and samples varied from 90 mg by less than 5 mg (5%). The samples were then homogenized in 5-sulfosalicylic acid (5% w/v). Homogenates were centrifuged for 5 min in a microfuge at 10,000 x g. The assay was carried out using the supernatants on the same day according to the methods of Anderson (12). Values are expressed as µmol per g/wet tissue.

Tissue Glutathione Assay

Ninety milligrams of mouse heart or liver were homogenized in 5-sulfosalicylic acid (5% w/w). Homogenates are centrifuged for 5 minutes in a microfuge at 10,000 x g. The assay is carried out using the supernatants on the same day according to the method of Anderson (12), Values are expressed as µmol/g wet tissue.

Figure 1:
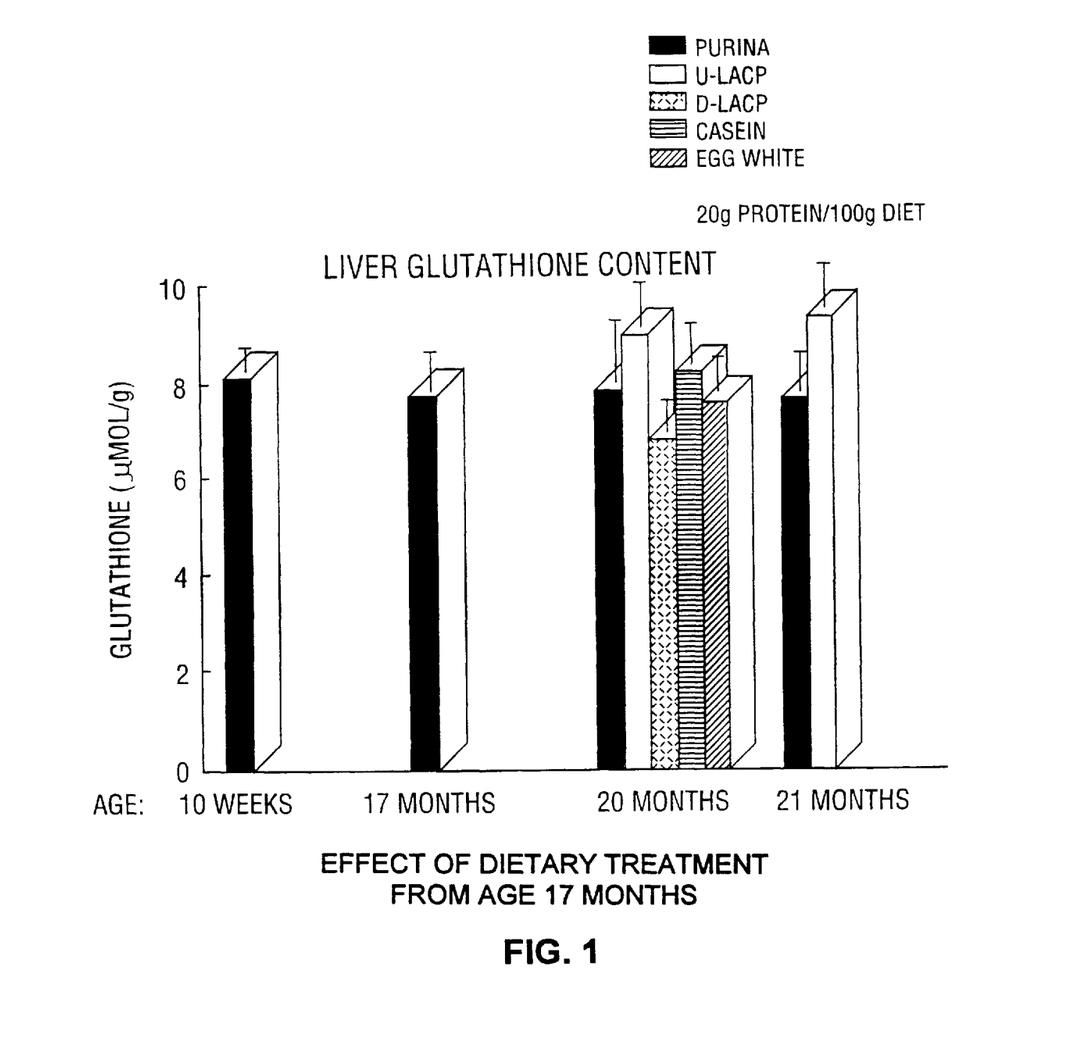
FIG. 1 illustrates the liver glutathione content in male mice C57BL/6NIA fed undenatured whey protein (U-Lacp), denatured whey protein (D-Lacp), casein, egg white protein or Purina diet-fed counterparts at age 10 weeks, 27, 20 and 21 months.
Figure 2:
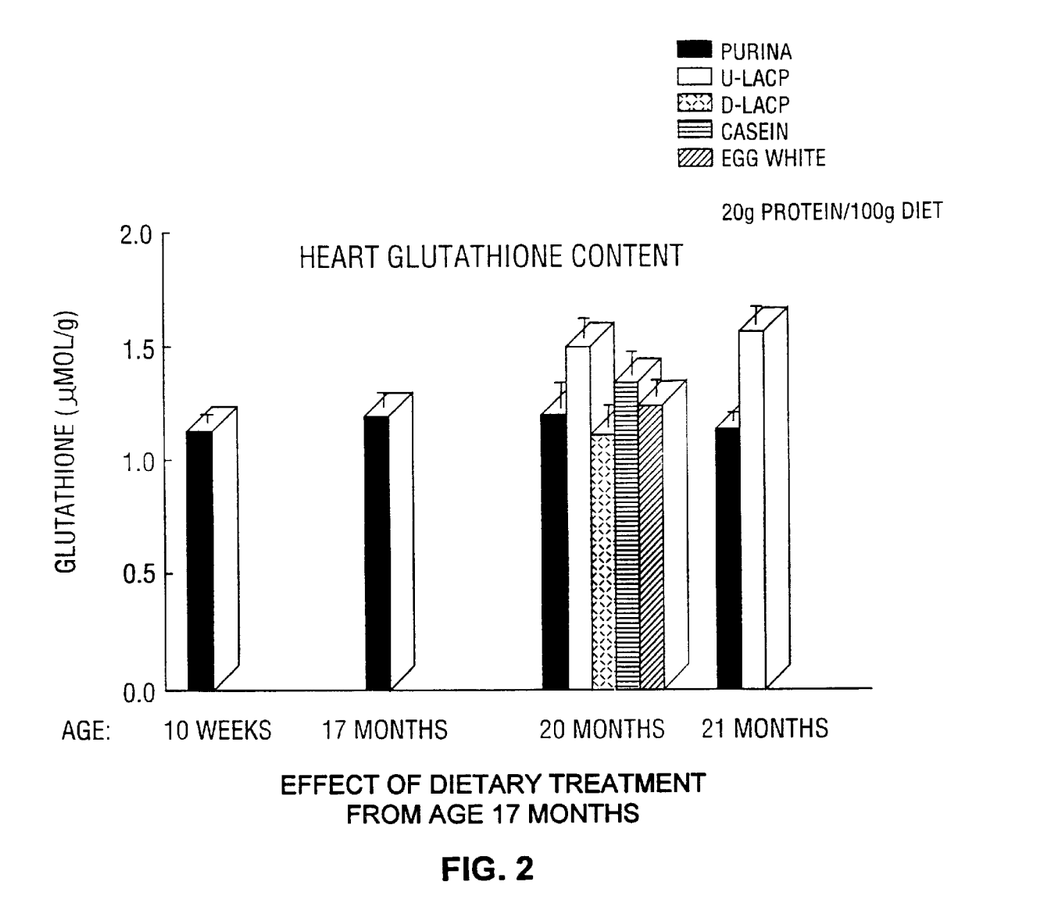
FIG. 2 illustrates the heart glutathione content of male mice C57BL/6NIA fed undenatured whey protein (U-Lacp), denatured whey protein (D-Lacp), casein, egg white protein or Purina diet-fed counterparts at age 10 weeks, 17, 20 and 21 months.

After three months on either diet initiated at age 17 months, GSH content was found to be higher in the liver and heart of U-Lacp (undenatured whey protein Lacprodan-80) fed mice compared to the D-Lacp (denatured whey protein Lacprodan-80), casein, egg white protein or Purina diet-fed counterparts (FIGS. 1 & 2). The GSH values in heart and liver of mice fed Purina laboratory chow was similar at age 10 weeks, 17, 20, 21 months. The U-Lacp diet appears to enhance the GSH content of heart and liver above "normal" values after 3 and 4 months of continuous feeding (FIGS. 1 & 2).

In addition, after three weeks on the U-Lacp diet, spleen GSH content is increased during the antigen driven clonal expansion of the lymphocytes in young adult C3H/HeN mice as compared to a decline in controls fed D-Lacp, casein or egg white protein diets. In old C57BL/6NlA mice, long term feeding of U-Lacp diet results in a moderate but sustained increase in liver and heart GSH levels (FIGS. 1 and 2). The GSH enhancing activity of WPC is restricted to its undenatured form (U-Lacp).

TABLE 2

AMINO ACID COMPOSITION
(g/100 g protein)

| Amino Acid | Whey Protein Concentrate* | Egg White Protein** |
|---|---|---|
| Aspartic acid | 11.3 | 7.9 |
| Threonine | 7.2 | 4.4 |
| Serine | 6.1 | 7.9 |
| Glutamic acid | 20.1 | 14.1 |
| Proline | 6.6 | 3.8 |
| Glycine | 2.0 | 3.7 |
| Alanine | 5.4 | 7.6 |
| Valine | 6.5 | 7.8 |
| Isoleucine | 6.7 | 6.5 |
| Leucine | 11.2 | 8.8 |
| Tyrosine | 2.9 | 4.2 |
| Phenylalanine | 3.1 | 6.4 |
| Lysine | 9.5 | 6.0 |
| Histidine | 1.9 | 2.2 |
| Arginine | 2.7 | 5.9 |
| Methionine | 2.2 | 3.9 |
| Cysteine | 2.4 | 2.4 |
| Tryptophan | 1.7 | 1.5 |

*Lacprodan-80 from Danmark Protein A/S, Copenhagen,. Denmark, 1986; used in these experiments.
**Values calculated from "Amino Acid Content of Foods", U.S.D.A., 1957. Values from cysteine analyzed by Sigma on samples used = 2.38 g/100 g protein and in our laboratory = 2.4 g/100 g protein.

This property is not solely due to the high cysteine content of WPC because another protein source with similar cysteine content (egg white) (see Table 2) does rot exhibit this biological activity. This property of U-Lacp does not depend specifically on its nutritional efficiency as evaluated by body weight, serum proteins, and food consumption, but appears to depend on the primary, secondary and tertiary structure of the protein in its native form.

Some of the previously discussed methods of increasing intracellular levels of glutathione concentration are either toxic (13) or dangerous owing to the risks related to the initial phase of glutathione depletion (14, 15). The methods involving the use of gamma-glutamylcysteine (16), athiazolidine (17) or glutathione esters (18) (U.S. Pat. No. 4,784, 685) offer an interesting possibility for short term intervention. However, their long term effectiveness in producing sustained elevation of cellular glutathione has not been shown, nor has the possible toxicity of their long term use been disproved. Indeed, glutathione and glutathione disulfide were found to be positive in the most commonly used short term tests for carcinogenicity and mutagenicity (13). Relevant to our invention are recent data indicating specifically that a lack of the GSH precursor, cysteine, rather than a decrease in biosynthetic enzyme activities is responsible for the deficiency of GSH noted in aging animals (19). Similarly, the fall in cytosolic GSH in the liver of chronic ethanol fed rats does not appear to be caused by a limitation in the capacity of gamma-glutamylcysteine synthetase activity (20).

Data in FIGS. 1 and 2 show that the concentration of liver and heart glutathione in control Purina fed mice remains very constant over time. On the other hand a moderate but sustained elevation of tissue GSH was noted in mice fed the nutritionally equivalent whey protein (U-Lacp) diet. Only minuscule quantities of glutathione and no breakdown products that can be readily attributed to glutathione are excreted in urine (21). The magnitude of change in cellular glutathione concentration that can be achieved may be quite limited, perhaps reflecting the critical importance of this molecule and the attendant tight regulatory control. Glutathione itself serves as a negative feedback on the GSH synthetic enzymes, which obviously limits cellular capacity to increase GSH concentration (22). Glutathione reductase maintains GSH in its predominant reduced form ($\geq 90\%$). This serves both to maintain this functional state and also to control cellular concentration since reduced glutathione (GSH) cannot cross the membrane, whereas the oxidized form (GSSG) can and does afflux, resulting in decreased total glutathione. Besides these enzymes, gamma glutamyl-transpeptidase (GGT) is important in GSH metabolism. GGT serves as a salvage pathway for glutamyl moieties at the cell membrane level, passing them back into the cytosol to be used in GSH synthesis. Increased activity of this enzyme has been associated with elevated GSH concentration in a number of cell lines and malignant tissues (23, 24).

It is advantageous to include Vitamin $B_1$ (thiamine) in a diet that results in elevated GSH. Thiamine is involved in the transketolase reaction of the pentose phosphate shunt yielding NADPH (GSSG is reduced back to GSH by NAPPH; GSH reductase).

Vitamin $B_2$ (riboflavin) is also an advantageous addition. Flavin mononucleotide (FMN) and flavin adenin dinucleotide (FAD) are synthetized sequentially from riboflavin and are involved in GSH reductase.

Some milks, especially those from New Zealand, are low in selenium. Selenium is contained in GSH peroxidase. Mammals deficient in selenium have markedly decreased peroxidase activity. Therefore glutathione formation which is advantageous for its anticancer effect requires an adequate level of selenium.

If we assume a dosage level of 60 grams undenatured whey protein as a daily intake, the recommended levels of Vitamin $B_1$, Vitamin $B_2$ and selenium are as follows:

Vitamin $B_1$ 1.5–2.0 mg
Vitamin $B_2$ 1.7–2.2 mg
Selenium Methionine 40 mcg.–60 mcg.

The effects of a small increment in cellular GSH are greater than expected. For example, there are many reports of human and murine tumour cell lines selected in vitro for resistance to a variety of chemotherapeutic agents. In a number of these cell lines cellular GSH is increased consistently by 2-fold compared to the drug sensitive parental cell line, despite the fact that the level of drug resistance is often much greater, e.g. as much as 30-fold (24, 25, 26). In these cell lines, depletion of cellular GSH by selective inhibition of synthesis restores drug sensitivity to the resistant cells. This is effective only if the GSH depletion is maintained throughout the drug-treatment period.

Given the fact that cellular GSH is very tightly regulated, that a 2-fold increase may be maximal, and that the effect of small increments in GSH may be amplified by a variety of GSH-utilizing enzymes (e.g. glutathione peroxidase, glutathione-S-transferase), the reproducible change in GSH concentration observed in animals fed the whey-rich diet is likely to have biological importance. The chronic nature of this augmentation may contribute significantly to this effect.

Our findings show that in mice fed a casein diet the number and size of DMH induced colon carcinoma were reduced by a factor of 0.3 and 0.4 respectively in comparison to Purina fed controls (Table 3, below). However, in mice fed the whey protein diet with similar nutritional efficiency the number and size of DMH-induced colon carcinoma were reduced four fold in comparison to the Purina fed controls (Table 3, below). DMH-induced colon tumours appear to be similar to those found in humans as far as type of lesions and chemotherapeutic response characteristics are concerned (27, 28).

The superiority of the anti-cancer effect of whey protein in comparison to casein has been reported in our previous study (1). About 80% of the proteins in bovine milk are caseins and the remaining 20% are whey proteins (29, 30). In addition, using the traditional process of preparing casein, the amount of whey protein co-precipitated along with the casein varies from about 40 to 60% of the total amount of whey protein present in the milk (31). Therefore it is conceivable that the minor anti-cancer effect seen with casein could be due to the relatively (to caseins) small amount of whey protein coprecipitated with it. It is apparent from the above described studies that the antitumour activity of the dairy products is in the protein fraction and more specifically, as our invention demonstrates, in the whey protein component of milk.

The beneficial effect of this dietary WPC supplement is enhanced to the extent that it is a replacement for some or all of the patient's protein intake from other sources.

SURVIVAL STUDIES

Figure 3:
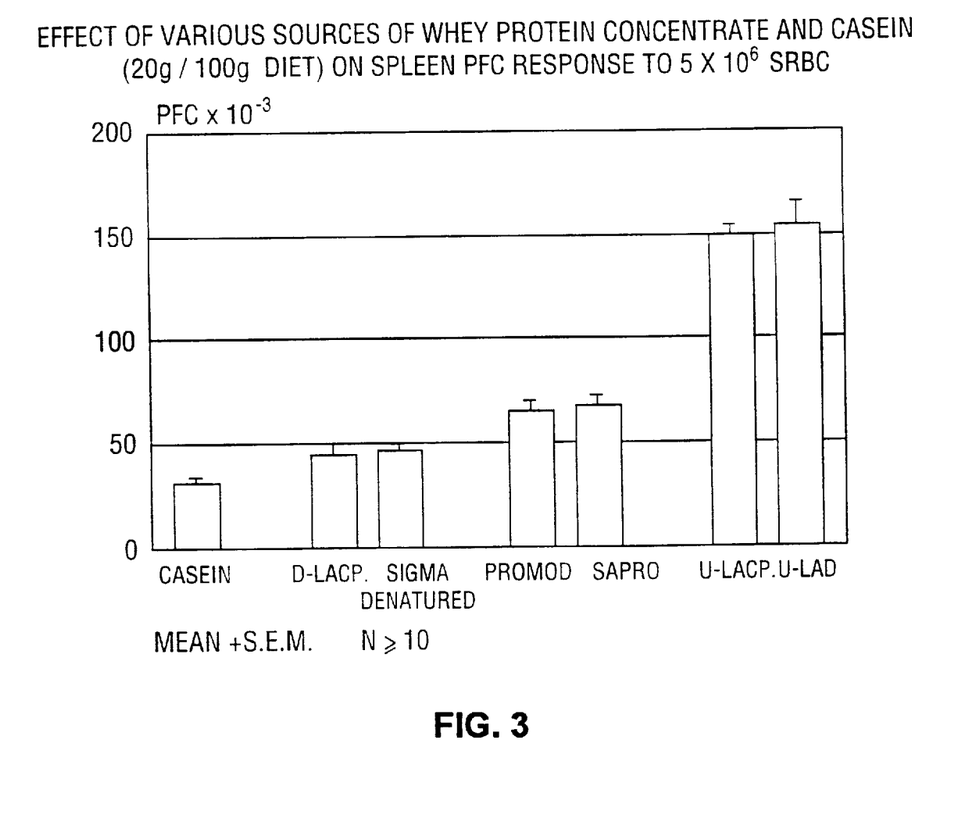
FIG. 3 illustrates the effect of various sources of whey protein concentrate and casein (20 g/100 g. diet) on spleen PFC response to $5 \times 10^6$ SRBC in mice.

The Biological Activity is Dependent on the Undenatured Conformation of WPC (a) Survival of Old Mice During a Limited Time Period:

Our study shows that the mean survival time, over a limited observation period of 6–7 months ending when 55% of male C57BL/6NlA mice were dead, is increased by about 30% in mice commenced on the undenatured whey protein (U-Lacp) diet at the onset of senescence (age 21 months) in comparison with "controls" fed the nutritionally equivalent Purina mouse chow. The survival curve of Purina fed mice was very similar to that of casein diet-fed mice. However, in the subsequent four months, mice on undenatured whey protein diet were switched to a denatured whey protein concentrate (D-Lacp) diet. During this period, the time of death of the remaining whey protein diet-fed mice became similar to that of their casein diet or Purina-fed counterparts. Throughout the study repeat bioassays of PFC formation confirmed the correlation between host immunoenhancement and undenatured state of WPC in diet as indicated in FIG. 3. In the second part of the study, when the difference between survival curves began to narrow, the immunoenhancing property of WPC was absent although its nutritional quality was preserved (D-Lacp). Throughout the entire study no significant intergroup difference was seen in calorie intake, and body weight. Since longevity is dependent primarily upon the genome of the individual it is unlikely that delayed mortality over a limited period of time would have influenced overall longevity.

TABLE 3

Effect of dietary milk protein on animal growth and tumour development in A/J mice treated with the carcinogen 1,2-Dimethylhydrazine.

|  | Whey Prot. 28 Weeks[a] | Casein 28 Weeks[a] | Purina 28 Week[a] | Pur/Whey 20/8 Weeks[b] | Pur/Cas 20/8 Weeks[b] |
|---|---|---|---|---|---|
| Initial Weight[c] (g) | 21.7 ± 0.5 | 21.5 ± 0.7 | 21.9 ± 0.8 | 21.9 ± 0.4 | 22.0 ± 0.7 |
| Final Weight[c] (g) | 21.5 ± 0.3 | 21.8 ± 0.4 | 19.7 ± 0.7 | 21.3 ± 1.0 | 21.0 ± 0.6 |
| Number of Tumours[c] | 8.4 ± 1.5 | 24.7 ± 3.0 | 35.9 ± 2.6 | 15.1 ± 3.2 | 21.7 ± 4.3 |
| Tumour Area[c] | 38.8 ± 6.4 | 90.9 ± 10.6 | 160.0 ± 11.4 | 47.9 ± 10.4 | 77.7 ± 10.9 |

[a]) Mice treated with DMH for 24 weeks, and then sacrificed 4 weeks later.
[b]) Mice treated with DMH for 24 weeks, and then sacrificed 4 weeks later. They were maintained on Purina Mouse Chow for 20 weeks and then switched to either Whey Protein or Casein diet for the remaining 8 weeks.
[c]) Mean ± SEM.
ANOVA: solid line(s) connect those means not significantly different ($p < 0.05$).

| Group | Whey | Pur/Whey | Pur/Casein | Casein |
|---|---|---|---|---|
| Number of Tumours |  | ———————— |  |  |
| Tumour Area |  | ———————— |  |  |

However, at least in terms of the immunoenhancing effect of the diet, this study could be regarded as a single direction cross-over from test (ULacp) to control (D-Lacp) diets, showing that the biological activity of WPC on survival of old mice is dependent upon its undenatured state and correlating directly with the PFC assay used in our study (as illustrated in FIG. 3).

(b) Short and Long Term Survival of Mice with DMH-Induced Colon Cancer:

In DMH treated mice we noticed a difference between mortality by the 28 weeks end point and the survival time to the end of the experiment in relation to dietary protein type. During the first seven months of study, the mice fed undenatured whey protein (U-Lacp) had no death as compared to a 33% mortality observed towards the end of this period in the casein and Purina groups. In the subsequent four months mice on whey protein were fed denatured whey protein (D-Lacp). During this latter period the D-Lacp diet appeared to have no favourable effect on survival in comparison to the casein diet (Table 4, below).

Throughout the study repeat bioassays of spleen PFC were done to document the physiologic effects of the diets on immune function as reported previously and the stability of these effects. The immunoenhancing effect of the U-Lacp diet was consistently confirmed for the first 7 months of the study; however, in the following four months-(D-Lacp), the immunoenhancing effect previously observed in mice fed the U-Lacp diet was absent. The values of PFC response in relation to either the U-Lacp diet or the D-Lacp diet were consistent with those presented in FIG. 3. This study therefore confirms the hypothesis that the biological activity of WPC on survival of tumour bearing mice is dependent upon its undenatured state correlating directly with the PFC assay used in our study.

TABLE 4

Effect of dietary milk protein on short and long term survival in A/J mice treated with the carcinogen 1,2-Dimethylhydrazine for 24 weeks.

|  | DIETARY GROUP[b] | | |
|---|---|---|---|
|  | Whey Protein[d] | Casein | Purina |
| Mortality[a] at 28 weeks | 0% | 33% | 33% |
| Survival time[c] in weeks | 40 | 41 | 30 |

[a]significant by Chi Square analysis: Whey Protein vs. Purina vs. Casein $p<0.05$.
[b]Originally 12 mice per group.
[c]Survival time in weeks from the first dose of carcinogen. Whey protein and Casein differ significantly from Purina, Mantel-Cox test $p<0.01$.
[d]Undenatured Whey Protein used from weeks 3 to 28. Denatured Whey Protein used from weeks 28 until end.

The experiment referred to above which are summarized in Tables 3 and 4 used Lacprodan 80 as a source of undenatured WPC:

We now prefer to use a whey protein concentrate (WPC) in undenatured form prepared from milk treated in the most lenient way compatible with accepted standards of safety with regard to bacterial contamination. The extremely high solubility index indicated that the proteins present are essentially undenatured, hence demonstrating the leniency of the ultrafiltration process [31]. Although the proteins contained in the concentrates from the other commercially available sources examined were mostly in undenatured form, as indicated by the relatively high solubility of the concentrates, the content of serum albumin and immunoglobulins in these mixtures is below the level activity [31]. These very thermolabile proteins are denatured, hence precipitated and partially lost from whey when high pasteurization temperatures are utilized.

Our studies also showed that administration of S(n-butyl) homocysteine sulfoximine, which reduces splenic glutathione in half, significantly reduced the humoral immune response of whey protein-fed mice. This was taken as further evidence for the important role of glutathione in the immunoenhancing effect of dietary whey protein (32).

Tissue glutathione concentration may be increased by administration of gamma-glutamyl-cysteine. Intracellular glutathione increased in the kidney by about 50%, 40–60 minutes after subcutaneous (s.c.) injection in mice, returning to control values 2 hours later (33). The administered gamma-glutamylcysteine is transported intact into the cells, and serves as a substrate for glutathione synthetase (33).

Advances in amino acid sequencing of food proteins allowed us to investigate the occurrence of glutamylcysteine groups in whey protein and the possible relation to glutathione promotion. Indeed, whey protein concentrate from bovine milk contains substantial amounts of glutamylcysteine groups, unlike casein, which does not increase tissue glutathione when fed to mice (35). The glutamylcysteine groups are located primarily in the serum albumin fraction (six groups/molecule). Glutamylcysteine groups are extremely rare in animal and plant edible proteins. Extensive search of all available data on amino acid sequencing of edible proteins reveals that the Glu-Cys group with a disulfide link is indeed limited to some of the whey protein, and to the ovomucoid fraction of egg white which contains 2 of these groups in a 30,000 mol.wt.molecule (31).

Our recent (31) data further indicate that the humoral immune response is highest in mice fed a dietary whey protein concentrate exhibiting the highest solubility (undenatured conformation) and, more importantly, a greater relative concentration of the thermolabile bovine serum albumin ($\geq 10\%$) and immunoglobulins. In addition, the mice fed this type of whey protein concentrate exhibit higher levels of tissue GSH. The glutamylcysteine groups (rare in food protein) and the specific intramolecular bond as related to the undenatured conformation of the molecule are considered to be key factors in the glutathione-promoting activity of the protein mixture.

Recent experiments in Japan [36] showed that spleen cells of BALB/c male mice fed 25 g of our undenatured whey protein concentrate (WPC) (for which the Trademark name "Immunocal" has been applied) per 100 g diet for 4 weeks had an increased immune response to SRBC in vitro and a high content of L3T4+ cells ($12.58 \times 10^6 \pm 1.36$) than mice fed an isocaloric diet with 25 g. pure casein/100 g. diet ($3.69 \times 10^6 \pm 0.50$). Similarly, the speen L3T4+/LYt–2+ ratio was $1.36 \pm 0.07$ in undenatured WPC fed mice and $0.55 \pm 0.07$ in casein-fed controls ($P<0.001$). Conversely, the relatively high concentrations of the thermosensitive serum albumin and immunoglobulins resulting from the low degree of pasteurization of milk in our WPC, may reflect more closely the pattern of raw milk. These data lend support to the hypothesis that the thermolabile Glu-Cys containing proteins such as serum albumin in undenatured conformation are crucial elements for the biological activity of whey protein concentrate.

Suitable bovine whey protein concentrate (WPC) has been prepared by the "Service de recherche sur les aliments du Ministere de l'agriculture du Quebec" in St-Hyacinthe, Quebec, Canada, with the following characteristics: pure protein content 75% (the rest mostly lactose, some fat and moisture); solubility index: (pH 4.6); 99.5%. Protein composition as of total whey protein measured by polyacrylamide gel electrophoresis (31) was: beta-lactoglobulin $59.1 \pm 4.0$; alpha-lactalbumin: $6.6 \pm 0.7$; serum albumin: $9.7 \pm 1.0$; immunoglobulin $24.6 \pm 2.6$ (mean±SD). The solubility index should preferably be above 99%.

The serum albumin of about 10% of the total whey protein was almost twice the corresponding value found in other commercially available whey protein concentrates that have been examined. It is believed that a serum albumin level $\geq 10\%$ is highly advantageous to improving the immune system.

Serum albumin includes a substantial amount of glutamyl cysteine which is a substrate for glutathione synthesis in the body. The role of glutathione is discussed in detail in or article "The Biological Activity of Undenatured Dietary Whey Proteins: Role of Glutathione", *Clin. Invest Med* 14: 296–309, 1991 (31), which is incorporated by reference in its entirety.

Immunoglobulin in the range of about 25 to 30% of total whey protein is also important. Pasteurization at 72° C. for 13 seconds resulted in an immunoglobulin level of $28 \pm 2\%$. We have found it possible to achieve a serum albumin level as high as $14 \pm 1\%$ with milk pasteurized at 72° C. for 13 seconds.

Upon bacteriological analysis no staph, salmonella, *B cereus*, or *E coli* were isolated in either the WPC prepared by the "Service de recherche sur les aliments du Ministere de l'agriculture du Quebec" or in the sample pasteurized at 72° C. for 13 seconds. Other samples were prepared by heating the milk to 63° C. for 30 minutes, with good results.

30 ml of heparinized blood may be used to determine the glutathione content of blood mononucleated phosphate buffered saline adjusted so that there are $10^7$ cells per tube. After centrifugation 900 ml of water is added to the pellet to lyse all the cells. To each aliquot is added 30% sulfosalicylic acid for a final concentration of 3% in 1 ml. After 15 minutes incubation, the samples are centrifuged, and the clear supernatant is used for the biochemical assay according to the method of Anderson [37]. Values are expressed as nanomol (nMol) per $GSH/10^7$ cells. Blood lymphocyte subsets may be determined by flow-cytometry.

The total serum protein, including the albumins and the immunoglobulins may be determined by the Biuret method. The level of Immunoglobulin A (IgA), Immunoglobulin G (IgG) and Immunoglobulin M (lgM) may be measured by immunonephlometry.

The presence of glutamylcysteine groups in the serum albumin component of the whey protein concentrate is considered to be a key factor in the glutathione-promoting and immunoenhancing activity of the protein mixture of the undenatured WPC. Our laboratory studies indicate that whey protein concentrates from other sources did not produce significant biological activities even though they exhibited similar nutritional efficiency. The percent serum albumin concentration in these products is (as mean±SD) respectively: $4 \pm 1$ in Promod (Ross laboratories), $4 \pm 1$ in Alacen 855 (New Zealand Dairy), $4.8 \pm 1$ in Lacprodan-80 (produced from 1989 by Danmark Protein), $4 \pm 0.1$ in Sapro (Sapro, Montreal), $4 \pm 1$ in Savorpro-75 (Golden Cheese, Calif., USA), $5 \pm 1$ in Bioisolate (Lesueur, Isolates, Minn.) [8] and $4.3 \pm 1$ in Promix (Dumex, Quebec). Similarly, the content of the other thermolabile protein, immunoglobulin, was about half the value of the undenatured WPC used in this study.

The results indicate that undenatured whey proteins by providing specific fuel for glutathione replenishment in the immunocytes could represent an adjuvant to other forms of therapy.

Historically, and up until now, bacteria and spores in milk were reduced by thermal treatment (pasteurization). In order to be effective, that method inevitably produced denaturation, and hence subsequent precipitation and loss in the curd of a substantial amount of the most thermolabile and presumed biologically active fractions of serum albumin and immunoglobulin.

Our objective is to obtain a whey protein concentrate (w.p.c) containing the proteins in proportion and conformation as close as possible to that of raw milk, compatible with accepted safety standards of bacterial content. Up until now we have utilized the lowest acceptable level of heat treatment of milk in order to preserve thermolabile whey protein.

An alternative to heat treatment is a method based on membrane microfiltration. Utilizing Bactocatch (Alfa-Laval Ltd. Scarborough, Ontario) we can obtain a permeate by special membrane microfiltration of the skimmed milk whose bacteria content has been reduced to less than 0.5% of original input levels.

This permeate is then treated with rennet and the proteins in the whey supernatant concentrated by a lenient procedure to obtain the desired undenatured whey protein concentrate. The membrane microfiltration concept is an alternative to the heat treatment of milk as an appropriate way to preserve heat labile whey proteins, although techniques and equipment may be improved in time.

Tables 5 and 6 illustrate schematically a process to produce an improved undenatured WPC which we have referred to under the trademark Immunocal. Table 7 is a comparative chart showing the characteristics of Immunocal in comparison with the sources of WPC and showing also the consequences of 3 weeks dietary treatment.

We have concluded as a result of our work that undenatured whey protein concentrate (WPC) is of value in the prophylaxis of cancers, such as chemically induced cancer, typically such as colon cancer which is promoted by carcinogens such as dimethylhydrazine. It also is useful for the treatment of patients having cancer cells such as chemically induced cancer cells, to inhibit the replication of such cells. An approximate dosage for humans is in the range of about 8 to 40 grams daily and preferably 20 to 40 grams daily. It is particulary beneficial to administer 30 to 40 grams daily. It has been established that it is particularly advantageous to use WPC having a serum albumin in concentration of at least 10%±1. The serum albumin should be at least 9% and most preferably at least 9.5%.

As the published literature shows, tumors of the colon induced by dimethylhydrazine in experiments with mice are similar to cancer of the colon in humans in terms of the type of lesion and response to chemotherapy. (27,28).

The discovery that the granulocytes/lymphocytes (G/L) ratio is increased in terminal cancer cases and correlates with the patient's condition (38) has prompted an interest in the factors that might influence this important parameter.

TABLE 5

A SCHEMATIC REPRESENTATION OF THE PROCESS TO PRODUCE THE WPC WHICH WE PREFER TO AS IMMUNOCAL

Raw milk
↓
Skimmed at 35° C.    = → cream
↓
Skimmed milk pasteurized at 63° C. for 30 minutes.
↓
At 38° C.: Addition of rennet (20 ml/100 kilos), allowing the agitation to resolve at low speed.
↓        = → curd
Whey
↓
Filtered with cheese cotton to remove debris (45 minutes):
At 40° C.: Ultrafiltration (Romecon UFSI, polysulphone membrane, cut off 50,000, pore diameter 0.06 of an inch, surface 2–3 $m^2$).
: Diafiltration to wash out salts and lactose.
Whey Protein Concentrate
↓
Pasteurized at 63° C. for 30 minutes.
↓
At 40° C.:   Lyophylization (16 hours).
↓
Whey Protein Concentrate, Powder:

TABLE 6

ASSAY OF PRODUCT OF TABLE 5

| Polyacrylamide gel electrophoresis | Serum Albumin 10 ± 1% | β-Lactoglobulin 57.8 ± 0.9% |
|---|---|---|
| α-Lactalbumin 11.4 ± 0.6% | Immunoglubin 22 ± 0.7% | |

For example granulocyte depletion using extracorporeal circulation was found to significantly reduce the size of a transplanted tumor in rabbit (39). Recent experimental studies in mice suggested the possibility that the second parameter of the G/L equation could be influenced by dietary means. Mice fed whey protein concentrate prepared so as to preserve the most thermosensitive molecule of whey, such as serum albumins in their native undenatured form, exhibited an enhanced immune response (35) manifested, in part, by an increased resistance to pneumococcal infection (40,1) and carcinogen induction of cancer (1)

This is the product which we referred to as undenatured WPC. Increased immune reactivity of mice fed with undenatured WPC was found to persist in naive cells transferred in vitro (36). The serum albumin contains six glutamylcysteine groups (31) hence provides the specific substrate for the synthesis of glutathione (33, 34) (GSH). These groups are extremely rare in food proteins (31).

TABLE 7

PHYSICAL-CHEMICAL CHARACTERISITCS AND BIOLOGICAL ACTIVITY OF DIFFERENT TYPES OF WHEY PROTEIN CONCENTRATES

| | Undenatured conformation | Protein composition (% of total whey proteins) | | | Immuno-globulins | Effect of 3 weeks dietary treatment | | |
|---|---|---|---|---|---|---|---|---|
| | Solubility index (pH 4.6) | β-LG[a] | α-La[2] | SA[3] | | PFC[4] × $10^{-3}$ | Glutathione ($\mu$mol/g)[5] Liver | Heart |
| Immunocal | 99.5% | 57.8 ± 0.9 | 11.4 ± 0.6 | 10 ± 1 | 22 ± 0.7 | 148 ± 16 | 7.95 ± 0.40 | 1.15 ± 0.7 |
| Promod | 97% | 61 ± 3 | 20 ± 1 | 4 ± 1 | 15 ± 3 | 65 ± 14 | 6.64 ± 0.41 | 1.0 ± 0.7 |
| Alacen 855 | 97.1% | 62 ± 8 | 22 ± 3 | 4 ± 1 | 12 ± 6 | 66 ± 17 | 6.04 ± 0.36 | — |
| Lacprodan-80 | 96% | 62 ± 4 | 18 ± 2 | 4.8 ± 2 | 15 ± 4 | 44 ± 15 | 6.70 ± 0.20 | — |
| Sapro | 95% | 60 ± 3 | 21 ± 2 | 4 ± 1 | 14 ± 3 | 31 ± 8 | — | — |
| Savorpro-75 | 98% | 63 ± 3 | 20 ± 1 | 4 ± 1 | 13 ± 3 | 31 ± 8 | — | — |
| Biolosolate | 90.1% | 66 ± 4 | 15 ± 1 | 5 ± 1 | 12 ± 3 | 65 ± 20 | — | — |
| Casein | — | — | — | — | — | 35 ± 9 | — | 1.0 ± 0.8 |

Values are expressed as mean ± S.D.; 20 g protein/100 g diet.
[1]β-LG, β-Lactoglobulin
[2]α-La, Alpha-Lactalbumin
[3]S.A., Serum Albumin2
[4]Number of plaque-forming cells/spleen 5 days following immunization with a 5 × $10^6$ sheep red blood cells
— Signifies not done
*Please see test for statistical reference.

The favourable effect of undenatured WPC in animal experiments were associated with a sustained elevation of tissue glutathione levels (41). However, nowhere this effect was more evident than in the spleen cells during the antigen driven clonal expansion of the lymphocyte pool (32): these experiments clearly indicate that the immune enhancing activity i.e. increased lymphocyte proliferation of dietary undenatured WPC is related to the observed greater production of GSH in the lymphocytes in comparison to an actual GSH decrease noted in casein fed controls during a similar antigenic challenge (32). GSH, a tripeptide thiol found in virtually all cells, is the major free radical oxygen scavenger (42). More specifically, the GSH content of the lymphocytes appears to be correlated with the ability of oxidants and thiols to modulate their proliferation (43). In this sense modulation of intracellular GSH may affect immune responsiveness (44, 45).

These experiments further indicate that the enhancing effect of dietary whey proteins on the lymphocytes is particularly evident when the antigenic stimulus for active proliferation is present.

However, this unique relation between dietary undenatured WPC and lymphocytes production is also manifest in normal unimmunized mice. After three weeks of dietary regimen, the spleen weights, as well as the spleen weight: body weight ratio of mice fed 20 g or 30 g undenatured WPC/100 g diet were moderately higher than the corresponding values of mice fed nutritionally equivalent diets containing 20 g or 30 g of either casein, soy protein or fish protein/100 g diet (46). More specifically, the number of cells per spleen were higher in undenatured WPC fed mice than the corresponding values in mice fed equivalent amounts of casein, wheat, soy and fish protein (35).

A more detailed study revealed that the number of nucleated cells in the spleen of mice fed a 25% undenatured WPC diet was significantly higher than the corresponding values in mice fed a control 25% casein diet. Interestingly, the observed changes were specifically related to doubling of the T cell population: particularly the L3T4[+] subpopulation increased four fold, whereas the number of B-cells was unchanged (36). This later finding is consistent with other studies showing that the effects of undenatured WPC are not exerted centrally on the rate of primary B-lymphoctye production in the bone marrow and that the immune enhancing effect is specifically seen in response to T-cell dependent antigens (47).

The above described effect of undenatured WPC on the lymphocytes may well explain the observed inhibitory effect of this form of dietary regimen on experimental tumors. Recent experiments showed that continuous feeding of undenatured WPC in the diet inhibits the development (number and size) of tumors in the colon of mice over a period of 24 weeks of dimethylhydrazine (DMH) treatment (1). This antitumor effect could be caused by increased resistance of target cells to the carcinogen and/or a direct inhibitory effect of dietary undenatured WPC on tumor growth. A subsequent series of experiments (2) where animals were fed standard laboratory diet for the first 20 weeks of DMH and then switched to the undenatured WPC diet for the remaining 8 weeks of DMH treatment, clearly indicate an inhibitory effect of undenatured WPC feeding on cancer cells.

It is noteworthy that the enhancing effect of undenatured WPC on the peripheral lymphoid tissues of normal animals is not associated with significant changes in the total number of blood lymphocytes (36,46). The absence of variation in total number of circulating lymphocytes was also noted in healthy humans (Otsuka Pharmaceutical Co. Ltd.).

The induction of cellular GSH synthesis by the glutamyl-cysteine groups of undenatured WPC may constitute another interesting effect of this product in cancer patients. Indeed, the introduction of the cysteine delivery system OTZ (ozothiazolidine -4-carboxylate), while enhancing GSH levels in normal cells was found to result in feedback inhibition of the GSH cycle in human tumor cells (5).

A clinical trial was arranged in Japan by Otsuka Pharmaceutical Co. Ltd. The clinical team was directed by Dr. Masakazu Adachi. The clinical trial involved five patients who had an advanced stage terminal cancer. A summary report is reproduced below as Table 8 and laboratory data of hematocytes and glutathione levels are given in Table 9 for four of the patients. The dosage level for each patient was 30 grams per day.

As shown in Table 8 the lymphocyte number in all patients increased during the adminstration of the undenatured whey protein concentrate. Two other patients with an advanced stage had withdrawn from the trial because of digestive problems. Previous investigation had reported that once the lymphocyte number had dropped in cancer patients, the recovery of the lymphocyte number to a normal level may not be possible. The increase of the lymphocyte number is of importance because of its potentiality for improving the G/L ratio.

The results shown in Tables 8 and 9 may be contrasted with healthy individuals who (based on tests of 14 individuals) will usually have an glutathione PMN level of 0.34±0.02, a glutathione RBC level of 0.066±0.006, a WBC of 6640±1700, a lymphocyte number of 2200±460 a G/L ratio of 1.85±0.45 and Plt 25.4±3.3.

Table 10 shows the bacteriological analysis and also the protein distribution and solubility of the undenatured WPC used in the trials described in Tables 8 and 9.

In conclusion, it appears that the administration of WPC to cancer patients increases the number of blood lymphocytes and decreases the G/L ratio. The lymphocyte concentration, very low at the outset, tends to return towards normal values. On the basis of previously described experimental evidence (38,39), the observed effect of WPC suggests inhibition of cancer cell growth.

In tests of undenatured WPC subsequent to those described in Tables 8 and 9, the following observations were made:

(1) Patient F had solid tumors in her abdomen that could be identified by physical examination and she had received chemotherapy. She had difficulty in consuming the undenatured WPC and was about to withdraw from treatment. However it was found that as long as she was taking the undenatured WPC her lymphocyte number increased, and the increasing number of tumor markers even showed signs of decreasing.

TABLE 8

| Patient | Cancer | Recurrence | improvement or terminal stage exacerbation | | during undenatured WPC administration: | | | |
|---|---|---|---|---|---|---|---|---|
| | | | | | G/L | lymphocytes | GSH/lymphocytes | period |
| A | Gastric | peritonitis carcinomatosa | tumor ↑ ascites ↑ | (+) ileus | n.c. | 980 → 1400 | n.t. | 54 days drop out |
| B | Uterus lung meta. | primary tumor | scc. 26 → 100 p.s.: 0 | liver metastasis ↑ | n.c. | 960 → 1300 | 0.36 → 0.47 → 0.34 | 143 days unfavourable |
| C | Breast bone meta | bone meta. (radiation therapy) | improveoment p.s.: 0 | | 4.4 → 2.2 | 480 → 1250 | 0.33 → 0.43 | 133 days favourable |
| D | Lung brain meta | LN meta. bone meta | tumor ↑ disturbance of consiousness | (+) | 11.6 → 4.0 | 340 → 930 | 0.85 → 0.53 died 50 days later | 79 days after drop out |
| E | Esophag. LN meta. | — | lung metastasis | (+) | n.c. | 600 → 1000 | 0.26 → 0.46 → 0.27 | 56 days unfavourable |

TABLE 9

Lab Data of Hematocytes and Glutathione Level: Cancer

| Pre Immu | After | Patient | Cancer | Compli. | GSH/PMN | GSH/RBC | WBC | Lymp. | Gran. | G/L | RBC | Plt. | Mono. |
|---|---|---|---|---|---|---|---|---|---|---|---|---|---|
| 0 day | | C | Breast | L.C. | 0.33 | 0.075 | 26.9 | 4.8 | 20.9 | 4.4 | 356 | 9.5 | 1.2 |
| | 8 days | C | Breast | | 0.47 | | 25.1 | | | | | | |
| | 35 days | C | Breast | | 0.40 | 0.083 | 34.3 | 8.3 | 23.4 | 2.8 | 352 | 11.5 | 2.6 |
| | 77 days | C | Breast | | 0.43 | 0.095 | 32.6 | 8.1 | 22.1 | 2.7 | 357 | 10.0 | 2.4 |
| | 91 days | C | Breast | | 0.37 | 0.074 | 40.4 | 11.6 | 25.7 | 2.2 | 362 | 12.0 | 3.1 |
| | 119 days | C | Breast | | | 0.088 | 38.6 | 16.1 | 19.2 | 1.2 | 367 | 11.4 | 3.3 |
| | 133 days | C | Breast | | 0.31 | 0.090 | 40.0 | 12.5 | 24.5 | 2.0 | 359 | 10.7 | 3.0 |
| 26 days | | E | Esophag. | | 0.26 | 0.067 | 38.5 | 5.9 | 29.4 | 5.0 | 416 | 23.6 | 3.2 |
| | 0 days | E | Esophag. | | 0.46 | 0.078 | 48.2 | 6.8 | 38.6 | 5.7 | 401 | 24.8 | 2.8 |
| | 14 days | E | Esophag. | | 0.39 | 0.061 | 45.5 | 7.4 | 34.6 | 4.7 | 405 | 26.0 | 3.5 |
| | 42 days | E | Esophag. | | | 0.066 | 53.6 | 8.7 | 40.6 | 4.7 | 393 | 25.1 | 4.3 |
| | 56 days | E | Esophag. | | 0.27 | 0.066 | 57.8 | 0.5 | 43.0 | 4.1 | 408 | 25.1 | 4.3 |
| 5 days | | D | Lung | | 0.85 | 0.073 | 44.7 | 3.4 | 39.3 | 11.6 | 345 | 32.9 | 2.0 |
| | 15 days | D | Lung | | 0.46 | 0.072 | 51.3 | 6.2 | 39.5 | 6.4 | 292 | 28.2 | 5.6 |
| | 42 days | D | Lung | | 0.53 | 0.071 | 50.6 | 9.3 | 37.3 | 4.0 | 325 | 32.9 | 4.0 |
| 3 days | | B | Uterus | | 0.38 | 0.083 | 45.8 | 9.6 | 33.6 | 3.5 | 319 | 19.1 | 2.6 |
| | 10 days | B | Uterus | | 0.34 | 0.083 | 42.8 | 7.7 | 32.9 | 4.3 | 306 | 17.9 | 2.2 |
| | 18 day | B | Uterus | | 0.50 | 0.087 | 57.5 | 12.1 | 42.4 | 3.5 | 575 | 21.7 | 3.0 |
| | 45 days | B | Uterus | | 0.55 | 0.090 | 51.0 | 13.1 | 35.5 | 2.7 | 315 | 19.8 | 2.4 |
| | 87 days | B | Uterus | | 0.43 | 0.099 | 52.2 | 10.1 | 37.1 | 3.7 | 324 | 19.2 | 5.0 |
| | 101 days | B | Uterus | | 0.47 | 0.076 | 66.5 | 12.9 | 49.5 | 3.8 | 296 | 28.8 | 4.1 |
| | 129 days | B | Uterus | | | 0.086 | 72.0 | 13.7 | 53.0 | 3.9 | 258 | 28.6 | 5.3 |
| | 143 days | B | Uterus | | 0.34 | 0.092 | 77.3 | 13.3 | 58.7 | 4.4 | 267 | 30.9 | 5.3 |

TABLE 10

Undenatured WPC powder preserved at 4° C. in dry environment with 3 exposures at room temperature (22–25° C.) for about 4 days.

BACTERIOLOGICAL ANALYSIS

| Time after production | Staph. | Salmonella | B cereus | E coli | Coliforms |
|---|---|---|---|---|---|
| 4 days | 0 | 0 | 0 | 0 | <100/100 g |
| 14 months | 0 | 0 | 0 | 0 | <100/100 g |

Protein distribution (1) and solubility (2)

| Time after production | Solubility | Beta-Lactoglubulla | Alpha Lactalbumin | Serum albumin | Others (3) |
|---|---|---|---|---|---|
| 4 days | 98.9 | 59.1 ± 4.0 (4) | 6.6 ± 0.7 | 9.7 ± 1.0 | 24.6 ± 2.6 |
| 14 months | 99.0 | 58.9 ± 3.9 | 9.6 ± 1.1 | 9.6 ± 1.1 | 22 ± 2.9 |

(1) Months by polyacrylamide gel electrophoresis
(2) Solubility index (ph 4.6)
(3) Mostly immunoglobulin
(4) Mean ± SD (2) Patient G was treated for a local recurrence of cancer after radiation. She received radiation treatment in November, 1992. Administration of undenatured WPC commenced December 4. Her lymphocytes improved between December 3 and Jan. 20, 1993 from 960 to 1310. As of February 3 there was no recurrence and her lymphocytes were 1370 and G/L 3.1.

(3) Patient H had received radiation therapy for a local tumor. Administration of undenatured WPC was commenced Dec. 16, 1992. At that time, test results were as follows:

| WBC | 2700 |
|---|---|
| Lym. | 480 |
| G/L | 4.6 |
| P/t | 9.5 |

Results on December 24 were:

| CEA | 11.0 |
|---|---|
| WBC | 4320 |
| Lym. | 910 |
| G/L | 3.7 |
| P/t | 10.7 |

On January 20 results were:

| CEA | 7.1 |
|---|---|
| WBC | 3420 |
| Lym. | 830 |
| P/t | 11.5 |

On February 3 the results were:

| CEA | 5.2 |
|---|---|
| WBC | 3,300 |
| Lym. | 860 |
| G/L | 2.5 |
| P/t | 11.5 |

It was noted that progress of the patient was good.

(4) Patient "I" had received radiation therapy on mediastinum, on cervical and total brain. Administration of undenatured WPC was started on Dec. 1, 1992. His lymphocytes increased from 340 on November 26 to 930 on January 13. His G/L ratio decreased from 12.1 to 4.4 and WBC increased from 4500 to 5100.

REFERENCES

Which Are Incorporated by Reference in Their Entirety

1. Bounous, G., Papenburg R, Kongshavn, P. A. L., Gold, P, Fleiszer, D. (1988) "Dietary whey protein inhibits the development of dimethylhydrazine induced malignancy." Clin. Invest. Med. 11:213–217.
2. Papenburg R., Bounous, G., Fleiszer, D., Gold, P. (1990) "Dietary milk proteins inhibit the development of dimethylhydrazine-induced malignancy." Tumor Biology 11:129–136.
3. Bourtourault, M., Buleon, R., Samperez, S., Jovan, P., (1991) "Effet des proteines du lactoserum bovin sur la multiplication de cellules cancereuses humaines." C.R. Soc. Biol. 185:319–323.
4. Laursen, I., Briand, P., Lykkesfeldt, A. E., (1990) "Serum albumin as a modulator of growth of the human breast cancer cell line MCF-7." Anti-cancer Res. 10:343–51.
5. Russo, A., De Graff, W., Friedman, N., Mitchell, I., (1985) "Selective modulation of glutathione levels in human normal versus tumour cells and subsequent differential response to chemotherapy drugs." Cancer Res. 46:2865–48.
6. Baruchel, S., Wang, T., Farah, R., Batist, G., (1992) "Different effects of OTZ on organ GSH levels in rats bearing tumours".
7. Villadsen, British Patent 1,495,940 published Dec. 21, 1977 and entitled "Anti-Cancer Active Whey Fractions".
8. JOHN, A. M., BELL, J. M. Amino acid requirements of the growing mouse. J. Nutr. 106: 1361–1367, 1976
9. The mouse in biochemical research, Volume III, H. L. Foster, J. D. Small, J. D. Fox, editors, Academic Press, p.58, 1983.
10. HOAG, W. G., DICKIE, M. M. Nutrition in; *Biology of the laboratory mouse*, E. L. Green, editor, McGraw-Hill, New York, pp. 39–43, 1966.
11. CUNNINGHAM, A., and SZENBERG, A. Further improvements in the plaque technique for detecting single antibody forming cells. J. Immun. Vol 14, pg. 559–600, (1968)
12. ANDERSON, M. E. Tissue glutathione: In; *Handbook of methods for oxygen radical research.* C.R.C. Press, 317–329, 1985.

13. GLATT, H., PROTIC-SABLGIC, M., OESCH, F. Mutagenicity of glutathione and cysteine in the Ames Test. Science 220: 961–962, 1983.
14. TAYLOR, Y. C., BROWN, J. M. Elevation of intracellular glutathione levels following depletion and its relationship to protection against radiation and alkylating agents. Pharmacol. Ther. 39: 293–299, 1988.
15. WHITE, C. W., JACKSON, J. H., McMURTRY, I. F., REPINE, J. E. Hypoxia increases glutathione redox cycle and protects rat lungs against oxidants. J. Appl. Physiol. 65: 2607–2616, 1988.
16. ANDERSON, M. E., MEISTER, A. Transport and direct utilization of gamma-glutamylcyst(e)ine for glutathione synthesis. Proc. Natl. Acad. Sci. U.S.A. 80: 707–711, 1983.
17. WILLIAMSON, J. M., BOETTCHER, B., MEISTER, A. Intracellular cysteine delivery system that protects against toxicity by promoting GSH synthesis. Proc. Natl. Acad. Sci. U.S.A. 79: 6246–6249, 1982.
18. PURI, R. N., MEISTER, A. Transport of glutathione as gamma-glutamylcysteinyl-glycylester, into liver and kidney. Proc. Natl. Acad. Sci. U.S.A. 80: 5258–5260, 1987.
19. RICHIE, J. P., MILLS, B. J., LANG, C. A. Correction of a glutathione defiency in the aging mosquito increases its longevity. Proc. Soc. Exp. Biol. Med. 184: 113–117, 1987.
20. FERNANDEZ-CHECA, J. C., OOKHTENS, M., KAPLOWITZ. Effects of chronic ethanol feeding on rat hepatocyte glutathione. J. Clin. Invest. 83: 1247–1252, 1989.
21. LAUTERBURG, B. H., MITCHELL, J. R. Therapeutic doses of acetaminophen stimulate the turnover of cysteine and glutathione in man. J. Hepatol. 4: 206–211, 1987.
22. MEISTER, A., ANDERSON, M. E. Glutathione. Ann. Rev. Bloch. 52: 711–760, 1983.
23. MEKHAIL-ISHAK, K., HUDSON, N., TSAO, M. S., BATIST, G. Drug metabolizing enzymes in human colon cancer: Implications for therapy. Cancer Res. (In press), 1989.
24. LEWIS, A. D., HICKSON, I. D., ROBSON, C. N., HARRIS, A. L., ET AL. P.N.A.S. 85: 8511–8515, 1988.
25. HAMILTON, T. C., WINKLER, M. A., LOUIE K. G., BATIST, G., ET AL. Augmentation of adriamycin, melphalan and cisplastin cytoxicity in drug resistant and sensitive human ovarian cancer cell lines by BSO mediated GSH depletion. Biochem. Pharm. 34: 2583–2586, 1985.
26. SUZUKAKE, K., VISTICA, B. P., VISTICA, D. T. Dechlorination of L-phenylalanine mustard by sensitive and resistant tumor cells and its relationship to intracellular glutathione content. Biochem. Pharm. 32: 165–171, 1983.
27. ENKER, W. E., JACOBITZ, J. L. Experimental carcinogenesis of the colon induced by 1,2-dimethylhydrazine-di HCl: Value as a model of human disease. J. Surg. Res. 21: 291–299, 1976.
28. CORBETT, T. H., GRISWOLD, D. P., ROBERTS, G. J. ET AL. Evaluation of a single agent and combination of chemotherapeutic agents in mouse colon carcinogenesis. Cancer 40: 2650–2680, 1977.
29. WALSTRA; P. JENNEP. Dairy chemistry and physics. Wiley J. Nitork, (ed.), p. 106, 1984.
30. SWAISGOOD, M. E. Characteristics of edible fluids of animal origin: Milk, in; *Food Chemistry*, O. R. Fennema, (ed.)., Marcel Dekker, p. 796, 1985.
31. Bounous G,, Gold P: The biological activity of undenatured dietary whey proteins: role of glutathione. Clin Invest Med 14:296–309, 1991.
32. Bounous G,, Batist G,, Gold P: Immunoenhancing property of dietary whey protein in mice: Role of glutathione. Clin Invest Med 12:154–61, 1989.
33. Anderson M E, Meester A: Transport and direct utilization of gamma-glutazylcyst(e)ine for glutathione synthesis. Proc Natl Acad Sci 80:707–11,, 1983.
34. Meister A: 5-Oxoprolinuria and other disorders of glutathione biosynthesis. In: Stranbury J B, Wymgaarden J B, Frederikson D S, eds. Metabolic basis of inherited diseases 4th edn. McGraw Hill, 1978:328–35
35. Bounous G. Kongshavn P A L, Gold. P: The immunoenhancing property of dietary whey protein concentrate. Clin Invest Med 11:271–8, 1988.
36. Hirai Y,, Nakay S. Kikuishi H,, Kawai K; Report: Evaluation of the immunological enhancement activities of Immunocal. Otsuka Pharmaceutical Co. Ltd: Cellular Technology Institute: Dec. 13, 1990, Osaka, Japan.
37. Anderson M E: Tissue glutathione: In: C.R.C. Handbook of methods for oxygen radical research. Boca Raton, Fla.: CRC Press, Inc., 1985:317–29
38. IETOMI K. A study on the role of granylocytes in carcinoma-bearing hosts.
G/L ratio a new host indicator-J. Jpn Soc. Cancer ther. 25/662–671/1990
39. TABUCHI T., SOMA T., TONEKAWA M., KOMAI T., HASHIMOTO T., ADACHI M. "Reduction of V X 2 transplanted tumor by granulocyte depletion using extracorporeal circulation on rabbit models". Anticancer Res.
40. BOUNOUS G, KONGSHAVN P A L, GOLD P: Influence of protein type in nutritionally adequate diets on the development of immunity. In: Friedman M, ed. Adsorption and utilization of amino acids. Vol. II. Boca Raton, Fla.: C.R.C. Press, Inc., 1989: 212–33
41. BOUNOUS, G., GERVAIS R., AMER V., BATIST G., GOLD P., "The influence of dietary whey protein on tissue glutathione and the diseases of aging". Clin. Invest. Med. 12: 343–349, 1989.
42. RICHIE J. P. The role of glutathione in aging and cancer. Exper. Gerontology 27: 615–626, 1992
43. NOELLE R J, LAWRENCE D A: Determination of glutathione in lymphocytes and possible association of redox state and proliferative capacity of lymphocytes. Biochem J: 198: 571–9, 1981
44. FIDELUS R K, TSAN M F: Enhancement on intracellular glutathione promotes lymphocyte activation by mitogen. Cell Immunol 97: 155–63, 1986.
45. GOUGEROT-POCIDALO M A, PAY M, ROCHE S: Mechanisms by which oxidative injury inhibits the proliferative response of human lymphocytes to PHA, Effect of the thiol compound 2-mercapto-ethanol. Immunology 64: 281–8, 1988.
46. BOUNOUS G., LETOURNEAU L., KONGSHAVN P. A. L., "Influence of dietary protein type on the immune system of mice". J. Nutr. 113: 1415–1421, 1983
47. BOUNOUS G., SHENOUDA N., KONGSHAVN P. A. L., OSMOND D. G., "Mechanism of altered B-cell response induced by changes in dietary protein type in mice". J. Nutr. 115: 1409–1417, 1985

The embodiments of the invention in which an exclusive property or privilege is claimed are defined as follows:

1. A method of prophylaxis of colon cancer of the type induced by dimethylhydrazine in mammals comprising the administration to a patient of an undenatured whey protein concentrate containing at least 9.5% serum albumin, at a daily dosage in the range 8 to 40 grams.

2. A method for treating cancer, comprising administering to a patient having cancer an undenatured whey protein concentrate containing at least 9.5% serum albumin in amount sufficient to increase the lymphocyte number of the patient.

3. A method for treating cancer, comprising administering to a patient having cancer an undenatured whey protein concentrate containing at least 9.5% serum albumin in an amount sufficient to decrease the G/L ratio of the patient.

4. The method of any one of claims 2 or 3 in which the daily dosage level is in the range of 8 to 40 grams.

5. The method of any one of claims 2 or 3 in which the undenatured whey protein concentrate is prepared from milk and contains substantially all the proteins present in the raw milk.

6. The method of any one of claims 2 or 3 including administering, in addition, Vitamin $B_1$ in the amount of about 1.5 to 2.0 mg per 60 grams of undenatured whey protein concentrate.

7. The method of any one of claims 2 or 3 including administering, in addition, Vitamin $B_2$ in the amount of about 1.7 to 2.2 mg per 60 grams of undenatured why protein concentrate.

8. A method of treating cancer in a patient in need thereof comprising the administration to said patient of a substantially undenatured whey protein concentrate, which concentrate comprises substantially all thermolabile whey proteins of the source milk with glutamylcysteine groups and disulfide bonds, in an amount sufficient to replenish depleted intracellular glutathione, enhance immune response and exert anti-cancer effects.

9. A method of treating cancer in a patient in need thereof comprising the administration to said patient of a substantially undenatured whey protein concentrate, which concentrate comprises substantially all thermolabile whey proteins of the source milk with glutamylcysteine groups and disulfide bonds, in an amount sufficient to increase the lymphocyte number.

10. A method of treating cancer in a patient in need thereof comprising the administration to said patient of a substantially undenatured whey protein concentrate, which concentrate comprises substantially all thermolabile whey proteins of the source milk with glutamylcysteine groups and disulfide bonds, in an amount sufficient to decrease the G/L ratio of a patient having cancer.

11. A method of treating cancer in a patient in need thereof comprising the administration to said patient of a substantially undenatured whey protein concentrate, which concentrate comprises at least about 2.4 grams cysteine per 100 grams protein, in an amount sufficient to replenish depleted intracellular glutathione, enhance immune response and exert anti-cancer effects.

12. A method of claim 8, in which the serum albumin is at least 9.0%.

13. A method as in any one of claims 8 to 12, in which the daily dosage level is in the range of 8 to 40 grams.

14. A method as in claim 13, in which the daily dosage level is in the range of 20 to 40 grams.

15. A method as in claim 14, in which the daily dosage level is in the range of 30 to 40 grams.

16. A method of treating cancer in patients having lesions of the colon of the type induced by dimethylhydrazine and being in need of treatment comprising the administration to said patient of a substantially undenatured whey protein concentrate, which concentrate comprises substantially all thermolabile whey proteins of the source milk with glutamylcysteine groups and disulfide bonds, in an amount sufficient to replenish depleted intracellular glutathione, enhance immune response and exert anti-cancer effects.

17. A method as in any of claims 8 to 11 or 16 above, in which selenium is administered in the amount of about 40–60 mcg (calculated as selenium methionine) per 60 grams of undenatured whey protein concentrate.

18. A method as in any one of claims 8 to 11 or 16 above, in which Vitamin $B_1$ is administered in the amount of about 1.5–2.0 mg per 60 grams of undenatured whey protein concentrate.

19. A method as in any one of claims 8 to 11 or 16 above, in which Vitamin B2 is administered in the amount of about 1.7–2.2 mg per 60 grams of undenatured whey protein concentrate.

20. A method as in any one of claims 2, 3, 8 to 11 or 16 above, in which the following are administered per 60 grams of undenatured whey protein concentrate:

Vitamin $B_1$ about 1.5–2.0 mg
Vitamin $B_2$ about 1.7–2.2 mg and
Selenium 40–60 mcg (calculated as selenium methionine).

21. A method of prophylaxis of colon cancer of the type induced by dimethylhydrazine in mammals comprising the administration to a patient of an undenatured whey protein concentrate, which concentrate comprises substantially all thermolabile whey proteins of the source milk with glutamylcysteine groups and disulfide bonds, at a daily dosage in the range of 8 to 40 grams.

22. A method as in claim 20 in which the daily dosage level is in the range of 8 to 40 grams.

* * * * *